United States Patent
Weigand et al.

(10) Patent No.: US 9,151,872 B2
(45) Date of Patent: Oct. 6, 2015

(54) PHOTOCHROMIC DOUBLE-FUSED NAPHTHOPYRANS

(71) Applicants: Udo Weigand, München (DE); Herbert Zinner, Rohrbach (DE); Yven Rohlfing, München (DE)

(72) Inventors: Udo Weigand, München (DE); Herbert Zinner, Rohrbach (DE); Yven Rohlfing, München (DE)

(73) Assignee: Rodenstock GmbH, München (DE)

( * ) Notice: Subject to any disclaimer, the term of this patent is extended or adjusted under 35 U.S.C. 154(b) by 0 days.

(21) Appl. No.: 14/347,009

(22) PCT Filed: Sep. 26, 2012

(86) PCT No.: PCT/EP2012/004040
§ 371 (c)(1),
(2) Date: Mar. 25, 2014

(87) PCT Pub. No.: WO2013/040586
PCT Pub. Date: Apr. 4, 2013

(65) Prior Publication Data
US 2014/0235876 A1    Aug. 21, 2014

(30) Foreign Application Priority Data
Sep. 26, 2011  (DE) .......................... 10 2011 114 270

(51) Int. Cl.
| | |
|---|---|
| *G02B 1/04* | (2006.01) |
| *C07D 493/04* | (2006.01) |
| *C07D 493/14* | (2006.01) |
| *C09K 9/02* | (2006.01) |
| *C08K 5/156* | (2006.01) |
| *G02B 5/23* | (2006.01) |

(52) U.S. Cl.
CPC .............. *G02B 1/041* (2013.01); *C07D 493/04* (2013.01); *C07D 493/14* (2013.01); *C08K 5/156* (2013.01); *C09K 9/02* (2013.01); *C09K 2211/1088* (2013.01); *G02B 5/23* (2013.01)

(58) Field of Classification Search
CPC ...... C07D 493/04; C07D 493/14; C09K 9/02; G02B 1/041
USPC .......................................... 549/381
See application file for complete search history.

(56) References Cited

U.S. PATENT DOCUMENTS

| | | |
|---|---|---|
| 5,679,805 A | 10/1997 | Hughes |
| 7,544,315 B2 | 6/2009 | Melzig et al. |
| 8,236,716 B2 | 8/2012 | Melzig et al. |

FOREIGN PATENT DOCUMENTS

| | | |
|---|---|---|
| WO | 99/28323 A1 | 6/1999 |
| WO | 00/02884 A2 | 1/2000 |
| WO | 2006/045495 A1 | 5/2006 |
| WO | 2009/024271 A1 | 2/2009 |

OTHER PUBLICATIONS

International Search Report and Written Opinion of the International Searching Authority, PCT/EP2012/004040, Nov. 28, 2012.
English Translation of International Search Report of the International Searching Authority, PCT/EP2012/004040, Nov. 28, 2012.

*Primary Examiner* — Noble Jarrell
*Assistant Examiner* — John Mauro
(74) *Attorney, Agent, or Firm* — McDonald Hopkins LLC

(57) ABSTRACT

The present invention relates to photochromic double-fused naphthopyrans of the general formula (I) or (II) and the use thereof in plastics of all kinds, particularly for ophthalmic purposes. The photochromic compounds according to the invention are characterized by two distinct absorption bands of the open form in the visible wavelength range, i.e. two conventional photochromic dyes, each having only one discrete absorption band, can be replaced with dye molecules of this type. The compounds according to the invention, moreover, have a very good lifetime with a very high performance.

11 Claims, 2 Drawing Sheets

PHOTOCHROMIC DOUBLE-FUSED NAPHTHOPYRANS

This application is a 35 U.S.C. 371 national stage filing and claims priority to PCT Application No. PCT/EP/2012/004040, entitled "Photochromic doubly-fused naphthopyrans," filed Sep. 26, 2012, which claims the benefit of German Application No. 10 2011 114 270.7, entitled "Photochromic double-fused naphthopyrans" filed Sep. 26, 2011, both of which are incorporated by reference herein in their entirety.

The present invention relates to photochromic double-fused naphthopyrans of the general formula (I) or (II) and the use thereof in plastics of all kinds, particularly for ophthalmic purposes. The photochromic compounds according to the invention are characterized by two distinct absorption bands of the open form in the visible wavelength range, i.e. two conventional photochromic dyes, each having only one discrete absorption band, can be replaced with dye molecules of this type. The compounds according to the invention, moreover, have a very good lifetime with a very high performance.

There has long been knowledge of various dye classes which, on irradiation with light of particular wavelengths, especially solar rays, reversibly change color. This is because these dye molecules are converted by light energy to an excited state, which they leave again in the event of interruption of the energy supply and revert to their starting state. These photochromic dyes include various pyran systems which have already been described in the prior art with different base systems and substituents.

Pyrans, specifically naphthopyrans and larger ring systems derived from these, are currently the class of photochromic compounds which has been the subject of the most work. Even though a patent was first filed as early as 1966 (U.S. Pat. No. 3,567,605), it was not until the 1990s that compounds which appeared suitable for use in spectacle lenses were developed. Suitable classes of pyran compounds are, for example, the 2,2-diaryl-2H-naphtho[1,2-b]pyrans or the 3,3-diaryl-3H-naphtho[2,1-b]pyrans, which, in excited form, exhibit various colors, such as yellow, orange or red-orange.

A further class of photochromic compounds of interest is that of more highly fused pyrans which absorb at a longer wavelength owing to their larger ring system and give red, violet and blue hues. These may be systems derived either from the 2H-naphtho[1,2-b]pyrans or the 3H-naphtho[2,1-b] pyrans, which originate from the particular naphthopyran systems by fusion on the f side.

Diarylchromenes, especially naphthopyrans or heterocyclically fused benzopyrans, which are 6-substituted on the benzopyran by a phenyl ring or more generally an aromatic or heteroaromatic ring which is additionally bridged via the 5 position of the benzopyran via at least one carbon atom, oxygen atom or nitrogen atom, are currently the most promising photochromic compounds.

When this bridge is generated only via one atom, the result is a five-membered ring fused to the benzopyran. Examples of one carbon atom can be found in U.S. Pat. No. 5,645,767, U.S. Pat. No. 5,723,072 and U.S. Pat. No. 5,955,520, and examples of one oxygen atom in U.S. Pat. No. 6,018,059.

In U.S. Pat. No. 5,723,072, an unsubstituted, mono- or disubstituted heterocyclic ring may additionally be fused to this base system on the g, h, i, n, o or p side of the indenonaphthopyran. Accordingly, indeno[1,2-f]naphtho[1,2-b]pyrans with a very wide range of variation of possible substituents are disclosed.

WO 96/14596, WO 99/15518, U.S. Pat. No. 5,645,767, WO 98/32037 and U.S. Pat. No. 5,698,141 disclose photochromic indenofused naphthopyran dyes derived from 2H-naphtho[1,2-b]pyran, the compositions comprising them and a process for preparation thereof. In U.S. Pat. No. 5,698,141, an unsubstituted, mono- or disubstituted heterocyclic ring may additionally be fused to this base system on the g, h, i, n, o or p side of the indenonaphthopyran. The substituent list, which is very extensive in each case, also includes quite specific spiro compounds, more particularly those systems with a spiro heterocyclic group in which, including the spiro atom at the 13 position of the base system, a 5- to 8-membered ring which always contains two oxygen atoms is present. A further embodiment of the spiro ring can be found in Japanese application 344762/2000.

When this bond is generated via two atoms, the result is a fused six-membered ring with various options solely for C, O and N. Compounds with C=O and N—R (lactam bridge) are described in U.S. Pat. No. 6,379,591. Compounds with an unsubstituted $CH_2$—$CH_2$ bridge and a fused heterocycle in the 7,8 position of the parent benzopyran are disclosed in U.S. Pat. No. 6,426,023. U.S. Pat. No. 6,506,538 describes the carbocyclic analog compounds in which the hydrogen atoms in the bridge may be replaced by OH, ($C_1$-$C_6$)-alkoxy, or two hydrogen atoms on one carbon atom may be replaced by =O. U.S. Pat. No. 6,022,495 describes, inter alia, compounds having a O—$CR^1R^2$ bridge. WO 2009/024271 describes analogous compounds having an additional fusion on the upper benzene ring.

When this bond is generated by three atoms, the result is a fused 7-membered ring with very many possible variations through insertion of heteroatoms. Compounds with a $CH_2$—$CH_2$—$CH_2$ bridge are described in U.S. Pat. No. 6,558,583. Here too, the hydrogen atoms in the bridge may be replaced by OH, ($C_1$-$C_6$)-alkyl or ($C_1$-$C_6$)-alkoxy, or two hydrogen atoms on one carbon atom may be replaced by =O. Given the same substitution pattern, they absorb at a shorter wavelength than the fused 6-membered rings.

US 2004/0094753 describes both compounds with a diatomic and with a triatomic bridge. The diatomic (carbon) bridge is additionally fused to a carbo- or a heterocycle. The triatomic bridge contains three carbon atoms or two carbon atoms and one oxygen atom with no additional fusion. Both rings may bear various substituents.

The different photochromic dyes available in the prior art, however, have disadvantages which, when used in sunglasses, significantly impair the wear comfort of the wearer. Firstly, the dyes have insufficiently long-wave absorption in the excited state and in the unexcited state. Secondly, there is frequently too high a thermal sensitivity of the darkening, and lightening may at the same time be too slow. Furthermore, the dyes available in the prior art often have an inadequate lifetime and hence allow only a short service life of the sunglasses. The latter becomes perceptible in rapidly declining performance and/or significant yellowing. Common to the photochromic dyes in the prior art mentioned above is that they exhibit only one absorption band of the open form in the visible wavelength range. In order to achieve darkening phototropic glasses in neutral colors—i.e. in grey or brown hues—a balancing process between the different photochromic dyes of a mixture is required with respect to rate of lightening, lifetime and spectral excitation properties, so that the phototropic glass has the same hue at each time point of the darkening and lightening cycle. It would therefore be extremely valuable to be able to dispense with this balancing process.

Therefore, it is the object of the present invention to provide photochromic dyes which make it possible, in neutral colours—i.e. in grey or brown hues—to achieve darkening phototropic glasses with only one such photochromic dye.

Such photochromic dyes, moreover, should be characterized by the combination of a long-wave absorption maximum of the closed form with a steep edge to the visible wavelength range, high darkening performance, very rapid lightening reaction and very good light stability.

This object is achieved by the subject matter indicated in the claims.

In particular, the photochromic naphthopyrans having the general formula (I) or (II) are provided:

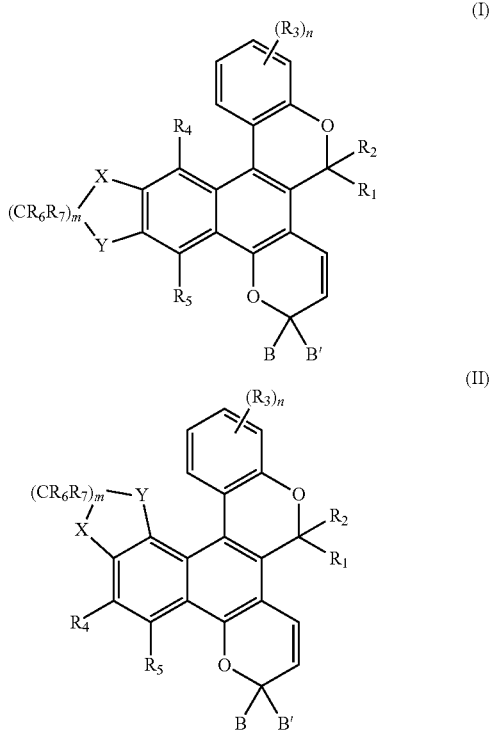

where the residues $R_1$, $R_2$, $R_3$, $R_4$ and $R_5$ are each independently a substituent selected from the group α, consisting of a hydrogen atom, a ($C_1$-$C_6$)-alkyl residue, a ($C_1$-$C_6$)-thioalkyl residue, a ($C_3$-$C_7$)-cycloalkyl residue, which may have one or more heteroatoms selected from O or S, a ($C_1$-$C_6$)-alkoxy residue, a hydroxyl group, a trifluoromethyl group, bromine, chlorine, fluorine, an unsubstituted, monosubstituted or disubstituted phenyl, phenoxy, benzyl, benzyloxy, naphthyl or naphthoxy residue, in which the substituents may in turn be selected from the group α, preferably from ($C_1$-$C_6$)-alkyl, ($C_1$-$C_6$)-alkoxy, bromine, chlorine or fluorine;
or
two residues $R_3$ (if in a position ortho to one another) are an unsubstituted, monosubstituted or disubstituted fused benzo, pyrido, naphtho, benzofuro or benzothieno ring, of which the substituents may be selected from the group α, preferably from ($C_1$-$C_6$)-alkyl, ($C_1$-$C_6$)-alkoxy, bromine, chlorine or fluorine;
n is an integer from 1 to 4,
X and Y are each independently selected from the group consisting of —O—, —S—, —N($C_1$-$C_6$)alkyl, —N$C_6H_5$, —CH$_2$—, —C(CH$_3$)$_2$— and —C($C_6H_5$)$_2$—,
the residues $R_6$ and $R_7$ in the —C$R_6R_7$— moiety are each independently a substituent selected from the group α, m is an integer from 1 to 4, particularly 1 or 2, or two or more adjacent —C$R_6R_7$— moieties are part of a fused benzene ring, which may be unsubstituted, monosubstituted or disubstituted, of which the substituents may be selected from the group α, preferably from ($C_1$-$C_6$)-alkyl, ($C_1$-$C_6$)-alkoxy, bromine, chlorine or fluorine, or
X and/or Y together with the respective adjacent —C$R_6R_7$ moiety are a fused benzene ring, which may be unsubstituted, monosubstituted or disubstituted, of which the substituents may be selected from the group α, preferably from ($C_1$-$C_6$)-alkyl, ($C_1$-$C_6$)-alkoxy, bromine, chlorine or fluorine,
and B and B' are each independently selected from one of the following groups a) or b), where
a) are mono-, di- and trisubstituted aryl residues, where the aryl residue is phenyl, naphthyl or phenanthryl;
b) are unsubstituted, mono- and disubstituted heteroaryl residues, where the heteroaryl residue is pyridyl, furanyl, benzofuranyl, thienyl, benzothienyl, 1,2,3,4-tetrahydrocarbazolyl or julolidinyl,
where the substituents of the aryl or heteroaryl residues in a) and b) are those selected from the previously defined group α or the group χ, consisting of amino, mono-($C_1$-$C_6$)-alkylamino, di-($C_1$-$C_6$)-alkylamino, mono- and diphenylamino unsubstituted, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, mono- or disubstituted phenothiazinyl, unsubstituted, mono- or disubstituted phenoxazinyl, unsubstituted, mono- or disubstituted 1,2,3,4-tetrahydroquinolinyl, unsubstituted, mono- or disubstituted 2,3-dihydro-1,4-benzoxazinyl, unsubstituted, mono- or disubstituted 1,2,3,4-tetrahydroisoquinolinyl, unsubstituted, mono- or disubstituted phenazinyl, unsubstituted, mono- or disubstituted carbazolyl, unsubstituted, mono- or disubstituted 1,2,3,4-tetrahydrocarbazolyl and unsubstituted, mono- or disubstituted 10,11-dihydrodibenz[b,f]azepinyl, where the substituents in turn may each independently be selected from ($C_1$-$C_6$)-alkyl, ($C_1$-$C_6$)-alkoxy, bromine, chlorine or fluorine;
or where two directly adjacent substituents of the aryl or heteroaryl residues in a) and b) are a V—(C$R_8R_9$)$_p$—W moiety, where p=1, 2 or 3, the residues $R_8$ and $R_9$ are each independently a substituent selected from the group α, and where V and W may each independently be —O—, —S—, —N($C_1$-$C_6$)alkyl, —N$C_6H_5$, —CH$_2$—, —C(CH$_3$)$_2$— or —C($C_6H_5$)$_2$—, where two or more adjacent C$R_8R_9$ units of this V—(C$R_8R_9$)$_p$—W moiety may be part of a benzene ring fused thereto, which in turn may each have one or more substituents selected from the group α, or V and/or W together with the respective adjacent C$R_8R_9$ unit is a fused benzene ring, which may be unsubstituted, mono- or disubstituted, of which the substituents may be selected from the group α.

Figure 1:
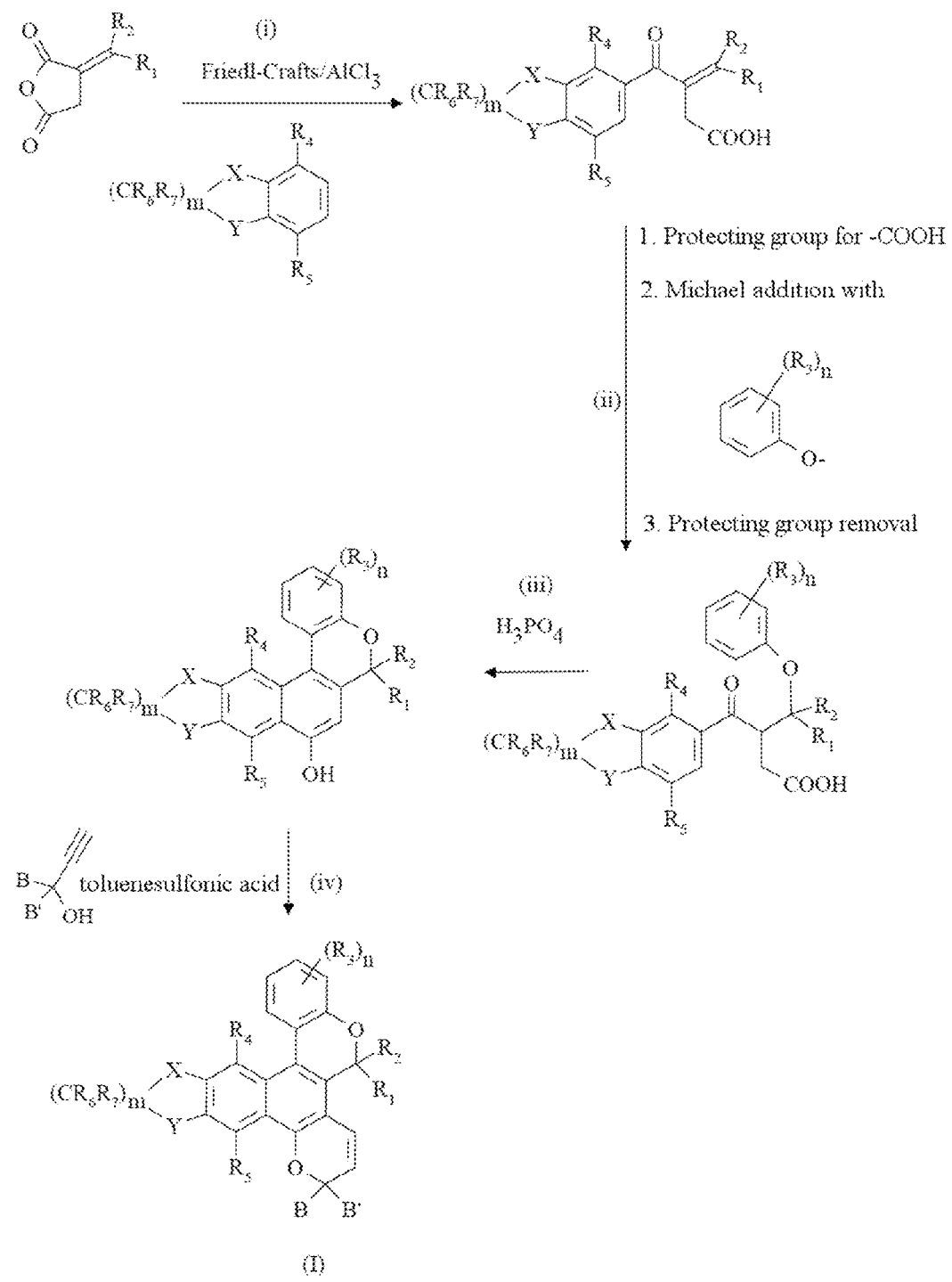
FIG. 1 shows a corresponding synthetic scheme for preparing the compounds according to the invention.

The compounds according to the invention, compared to the prior art (U.S. Pat. No. 6,022,495), are characterized by known photochromic fused 2H-naphtho[1,2-b]pyrans which exhibit a double absorption band, i.e. two bands, of the open form in the visible wavelength range, if a second fusion is introduced (cf. the ring unit with X and Y in the formulae (I) or (II) of the compounds according to the invention). The first of the two strong absorption bands has an absorption maximum of >500 nm while the maximum of the second band lies in the shorter wavelength visible range (400-500 nm). Owing to the latter band, it is possible with the compounds according to the invention to dispense with yellow- or orange-darkening photochromic dyes in neutral-color phototropic glasses.

Preferred photochromic naphthopyrans according to the present invention have the following general formulae (III), (IV) or (V):

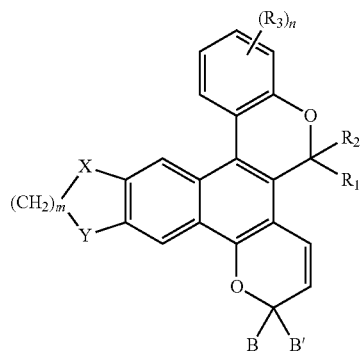
(III)

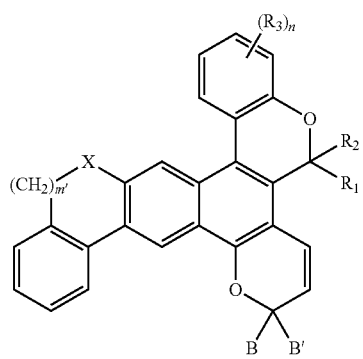
(IV)

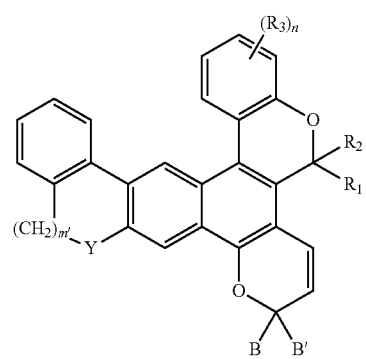
(V)

where X and Y are each independently selected from —O—, —NCH$_3$, —NC$_2$H$_5$, —NC$_6$H$_5$, —CH$_2$— or —C(CH$_3$)$_2$—, where the residues $R^1$ to $R^3$, B and B', m and n are as defined above, where m and n are preferably 1 or 2, m' is 0 or 1, with the proviso that either X or Y is oxygen in formula (III).

In a preferred embodiment, X and Y are both —O— in formula (III), where m is 1 or 2, preferably 2.

In another preferred embodiment, X is —O— and Y is —CH$_2$— or —C(CH$_3$)$_2$— in formula (III), wherein m is 1 or 2, preferably 2.

In another further preferred embodiment, X is —CH$_2$— or —C(CH$_3$)$_2$— in formula (IV), where m' is 0.

In another still further preferred embodiment, Y is —O— in formula (V), where m' is 1.

In a further preferred embodiment, Y is —NCH$_3$, —NC$_2$H$_5$ or —NC$_6$H$_5$ in formula (V), where m' is 0.

In a further preferred embodiment, the residues B and B' are each independently selected from the group a), as defined above.

The substituents of the group χ which have nitrogen atoms or bear amino groups are attached via the latter to the phenyl, naphthyl or phenanthryl residue of the group a).

With regard to the substituents of the group V—(CR$_8$R$_9$)$_p$—W moiety which may be attached to the phenyl, naphthyl or phenanthryl residue of group α) for the B or B' residues, when two or more adjacent carbon atoms of this V—(CR$_8$R$_9$)$_p$—W moiety may each independently be part of a benzo ring system fused thereto, this means that the two methylene carbon atoms (—CH$_2$—CH$_2$—) then become part of a fused ring system. When, for example, two or three benzo rings are fused, it is possible, for example, for the following structural units as shown below to be present:

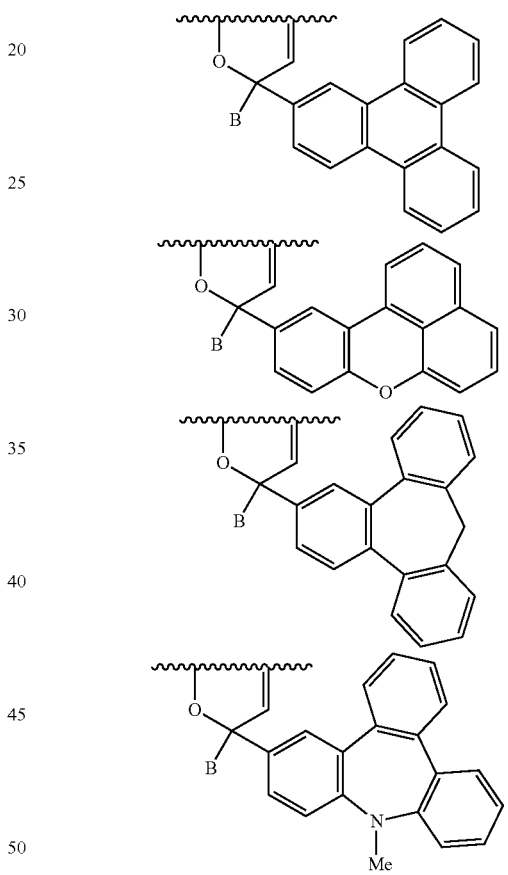

It will be appreciated, however, that it is also possible for only one benzo ring fused via two adjacent carbon atoms of this V—(CR$_8$R$_9$)$_p$—W moiety to be present.

Surprisingly, the compounds according to the invention, compared to the compounds from U.S. Pat. No. 6,022,495 as the prior art (i.e. compounds without the fused X and Y containing ring), have a second strong absorption band of the open form in the visible wavelength range (see FIG. 2). Interestingly, also in the compounds from WO 2009/024271, similar to the compounds of the present invention, which have a second ring fused at another position in the molecule, a second strong absorption band in the visible wavelength range cannot be observed. The formation of this second absorption band in the compound according to the invention is, in this respect, unexpected.

To measure the spectral properties of the compounds according to the invention, 350 ppm of each photochromic dye were dissolved in acrylate monomer matrix and, following addition of a polymerization initiator, were thermally polymerized with the aid of a temperature programme. The transmission properties in the excited state of the plastic lenses thus produced (thickness 2 mm) were subsequently analyzed according to DIN EN ISO 8980-3.

The first of the two strong absorption bands has an absorption maximum of >500 nm, while the maximum of the second band lies in the shorter-wave visible range (400-500 nm). Owing to the latter band, it is possible for the first time, with the compounds according to the invention, to dispense with yellow- or orange-darkening photochromic dyes for providing neutral-colored glasses. This is important on the one hand for polymer systems in which these yellow- and orange-darkening dyes—owing to their different molecular structure compared to the longwave absorbing violet- and blue-darkening dyes—have an insufficient lifetime or are accompanied by other disadvantages. On the other hand it is possible for the first time with the photochromic dyes according to the invention, in neutral colors—i.e. in grey or brown hues—to achieve darkening phototropic glasses with only one photochromic dye. The cumbersome balancing process between the different photochromic dyes of a mixture with respect to rate of lightening, lifetime and spectral excitation properties required to date is thus eliminated, so that the phototropic glass has the same hue at each time point of the darkening and lightening cycle.

Moreover, since the compounds according to the invention have a high clarity (i.e. high transmission in the non-excited state) and very good light stability, they are eminently suitable for use in phototropic glasses.

Figure 2:
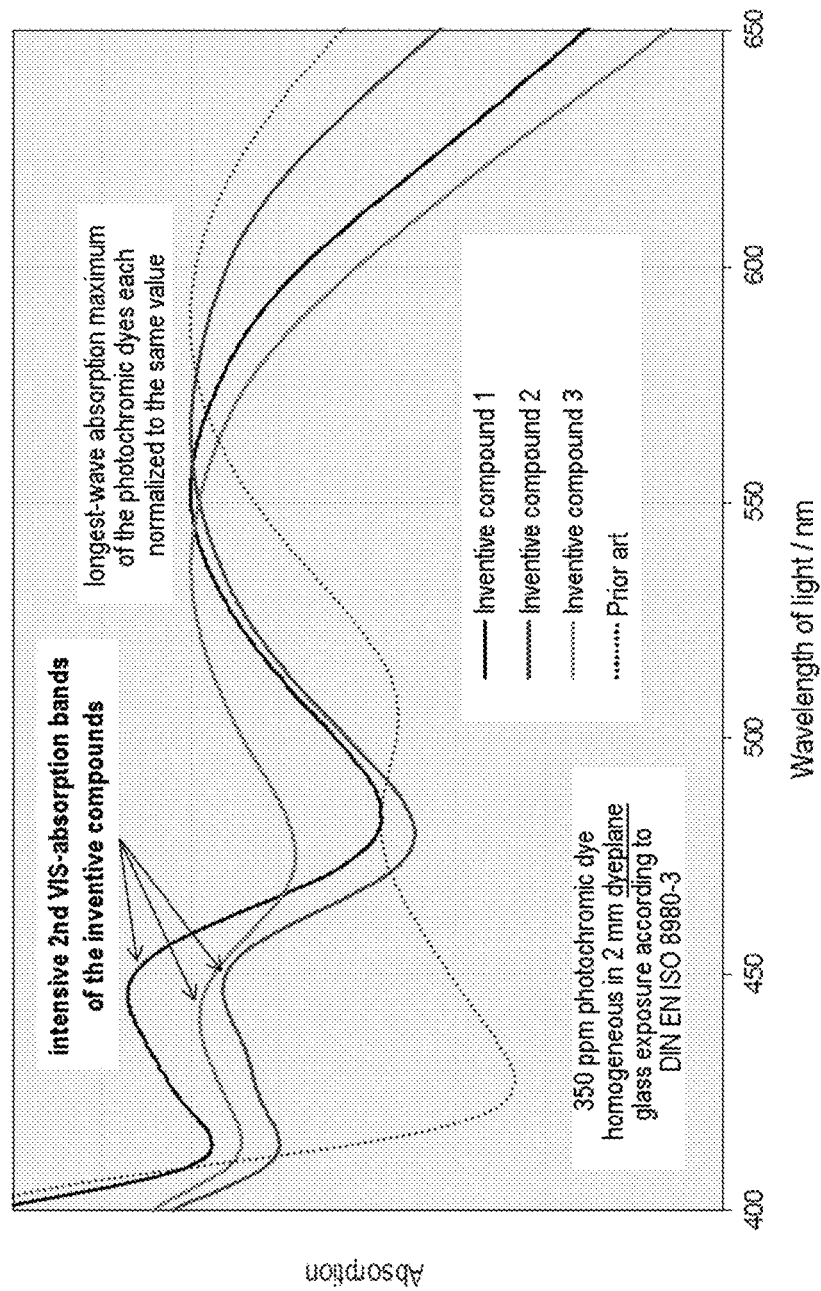
FIG. 2 shows the UV absorption spectra of specific compounds according to the invention in comparison with the prior art.

The structures of the compounds used or investigated in FIG. 2 are shown in the table below:

TABLE 1

Tabular comparison of the longest-wave absorption maximum in the excited state (An = anisyl, i.e. 4-methoxyphenyl)

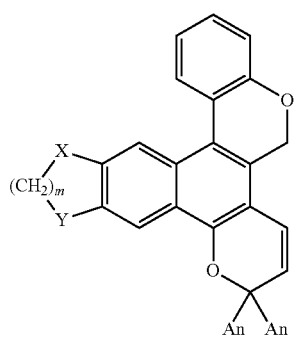

non-excited (colorless)

TABLE 1-continued

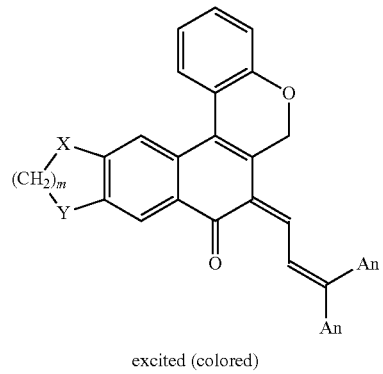

excited (colored)

| | X | $(CH_2)_m$ | Y | max (1) | max (2) | Color impression |
|---|---|---|---|---|---|---|
| Prior art U.S. Pat. No. 6,022,495 | — | — | — | — | 585 nm | Blue |
| Inventive compound 1 | O | $CH_2CH_2$ | O | 450 nm | 555 nm | Umber-brown |
| Inventive compound 2 | $CMe_2$ | ortho-phenylene | | 450 nm | 565 nm | (greenish) grey |
| Inventive compound 3 | O | $CH_2CH_2$ | $CMe_2$ | 445 nm | 545 nm | (reddish) brown |
| Inventive compound 4 | $CMe_2$ | $CH_2CH_2$ | O | 445 nm | 565 nm | neutral grey |

The optical color impression of the excited form is heavily dependent on the interval of the two absorption bands and their intensity ratio (see FIG. 2). Even minor shifts cause a significant change of the color impression.

To synthesize the compounds according to the invention, suitably substituted methylidenesuccinic anhydrides are subjected in a first step to a Friedel-Crafts reaction with suitably substituted fused aromatic compounds (step (i)). The COOH group of the resulting intermediate is subsequently protected and this intermediate is subjected to a Michael addition with appropriately substituted phenolate derivatives (step (ii)). After removal of the carboxylic acid protecting group, correspondingly substituted derivatives are formed via intramolecular cyclization using phosphoric acid (step (iii)). These substituted derivatives are then reacted with suitably substituted 2-propyn-1-ol derivatives to the inventive compounds according to step (iv). The abovementioned synthetic scheme is depicted in FIG. 1.

The compounds of formula (II) form as by-products in the course of the synthesis during the cyclization (iii) and may be isolated by suitable methods.

The compounds according to the invention may be used in plastic materials or plastic items of every type and form for a variety of purposes for which photochromic behavior is of interest. Here, a dye according to the present invention or a mixture of such dyes may be used. For example, the photochromic naphthopyran dyes according to the invention may be used in lenses, particularly ophthalmic lenses, lenses for spectacles of all types, such as ski goggles, sunglasses, motorcycle goggles, visors of helmets and the like. Furthermore, the photochromic naphthopyrans according to the invention can also be used, for example, as sun protection in vehicles and homes in the form of windows, protective screens, covers, roofs and the like.

For the preparation of such photochromic items, the photochromic naphthopyrans according to the invention can be applied to, or embedded in, a polymeric material, such as an organic plastic material, by various methods described in the prior art, such as already indicated in WO 99/15518.

We distinguish here between so-called mass coloring and surface staining procedures. A mass coloring procedure comprises, for example, the dissolving or dispersing of the photochromic compound or compounds according to the present invention in a plastic material, for example, by the addition of the photochromic compound(s) to a monomeric material before the polymerisation is carried out. A further possibility for producing a photochromic article is to permeate the plastic material(s) with the photochromic compound(s) by immersing the plastic material in a hot solution of the photochromic dye(s) according to the present invention or, for example, by a thermal transfer process. The photochromic compound(s) may also be provided, for example, in the form of a separate layer between adjacent layers of plastic material, for example, as part of a polymeric film. Further, it is also possible to deposit the photochromic compound(s) as part of a layer present on the surface of the plastic material. The term "permeation" here is intended to mean the migration of the photochromic compound(s) into the plastic material, for example, by the solvent-assisted transfer of the photochromic compound(s) in a polymer matrix, vapor phase transfer or other such surface diffusion processes. Advantageously, such photochromic articles, such as lenses, can be produced not only by means of conventional mass coloring, but also in the same manner by means of surface staining, where in the latter variant a surprisingly low migration tendency can be achieved. This is a particular advantage in the subsequent processing steps, since—for example, as with an antireflective coating due to the lower back diffusion in a vacuum—delamination and similar defects are drastically reduced.

Overall, based on the photochromic naphthopyrans according to the invention, any compatible (in chemical terms and in a color-dependent manner) stains, i.e. dyes, may be applied to, or embedded in, the plastic material in order to satisfy both aesthetic aspects and medical or fashion aspects. The specifically selected dye(s) may therefore vary, depending on the intended effects and requirements.

The invention claimed is:
1. Photochromic naphthopyrans having the general formula (I) or (II):

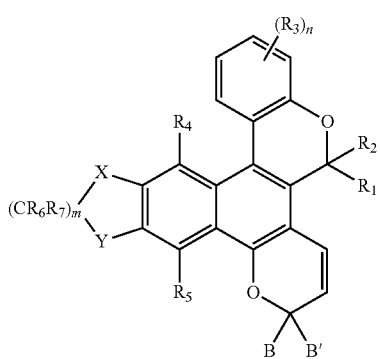

(I)

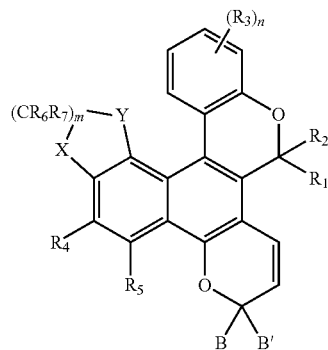

(II)

where the residues $R_1$, $R_2$, $R_3$, $R_4$ and $R_5$ are each independently a substituent selected from the group α, consisting of a hydrogen atom, a $(C_1\text{-}C_6)$-alkyl residue, a $(C_1\text{-}C_6)$-thioalkyl residue, a $(C_3\text{-}C_7)$-cycloalkyl residue, said $(C_3\text{-}C_7)$-cycloalkyl ring optionally having one or more heteroatoms selected from O or S, a $(C_1\text{-}C_6)$-alkoxy residue, a hydroxyl group, a trifluoromethyl group, bromine, chlorine, fluorine, an unsubstituted, monosubstituted or disubstituted phenyl, phenoxy, benzyl, benzyloxy, naphthyl or naphthoxy residue, in which the substituents in turn are optionally selected from a $(C_1\text{-}C_6)$-alkyl residue, a $(C_1\text{-}C_6)$-alkoxy residue, or a phenyl residue;

or two residues $R_3$ (if in a position ortho to one another) form an unsubstituted, monosubstituted or disubstituted fused benzo, pyrido, naphtho, benzofuro or benzothieno ring, of which the substituents are optionally selected from the group α;

n is an integer from 1 to 4,

X and Y are each independently selected from the group consisting of —O—, —S—, —N($C_1$-$C_6$)alkyl, —N$C_6H_5$, —$CH_2$—, —$C(CH_3)_2$— and —$C(C_6H_5)_2$—, the residues $R_6$ and $R_7$ in the —$CR_6R_7$ moiety are each independently a substituent selected from the group α, m is an integer from 1 to 4, or two or more adjacent —$CR_6R_7$ moieties are part of a fused benzene ring, which is optionally unsubstituted, monosubstituted or disubstituted, of which the substituents are optionally selected from the group α, or X and/or Y together with the respective adjacent —$CR_6R_7$ moiety are a fused benzene ring, which is optionally unsubstituted, monosubstituted or disubstituted, of which the substituents are optionally selected from the group α, and B and B' are each independently selected from one of the following groups a) or b), where a) are mono-, di- and trisubstituted aryl residues, where the aryl residue is phenyl, naphthyl or phenanthryl;

b) are unsubstituted, mono- and disubstituted heteroaryl residues, where the heteroaryl residue is pyridyl, furanyl, benzofuranyl, thienyl, benzothienyl, 1,2,3,4-tetrahydrocarbazolyl or julolidinyl, where the substituents of the aryl or heteroaryl residues in a) and b) are those selected from the previously defined group α or the group χ, consisting of amino, mono-$(C_1\text{-}C_6)$-alkylamino, di-$(C_1\text{-}C_6)$-alkylamino, mono- and diphenylamino unsubstituted, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, mono- or disubstituted phenothiazinyl, unsubstituted, mono- or disubstituted phenoxazinyl, unsubstituted, mono- or disubstituted 1,2,3,4-tetrahydroquinolinyl, unsubstituted, mono- or disubstituted 2,3-dihydro-1,4-benzoxazinyl, unsubstituted, mono- or disubstituted 1,2,3,4-tetrahydroisoquinolinyl, unsubstituted, mono- or disubstituted phenazinyl, unsubstituted, mono- or disubstituted carbazolyl, unsubstituted, mono- or disubstituted 1,2,3,4-tetrahydrocarbazolyl and unsubstituted, mono- or disubstituted 10,11-dihydrodibenz[b,f]azepinyl, where the substituents in turn are optionally each independently selected from $(C_1$-$C_6)$-alkyl, $(C_1$-$C_6)$-alkoxy, bromine, chlorine or fluorine;

or where two directly adjacent substituents of the aryl or heteroaryl residues in a) and b) are a V—$(CR_8R_9)_p$—W moiety, where p=1, 2 or 3, the residues $R_8$ and $R_9$ are each independently a substituent selected from the group α, and where V and W are each independently —O—, —S—, —N$(C_1$-$C_6)$alkyl, —$NC_6H_5$, —$CH_2$—, —$C(CH_3)_2$— or —$C(C_6H_5)_2$—, wherein two or more adjacent $CR_8R_9$ units of this V—$(CR_8R_9)_p$—W moiety are optionally part of a benzene ring fused thereto, and when part of benzene ring, each $CR_8R_9$ unit optionally has one or more substituents selected from the group α, or V and/or W together with the respective adjacent $CR_8R_9$ unit is a fused benzene ring, which is optionally unsubstituted, mono- or disubstituted, of which the substituents are optionally selected from the group α.

2. The photochromic naphthopyrans as claimed in claim 1 having the general formula (I), where m is 1 or 2.

3. The photochromic naphthopyrans as claimed in claim 1 having the following general formulae (III), (IV) or (V):

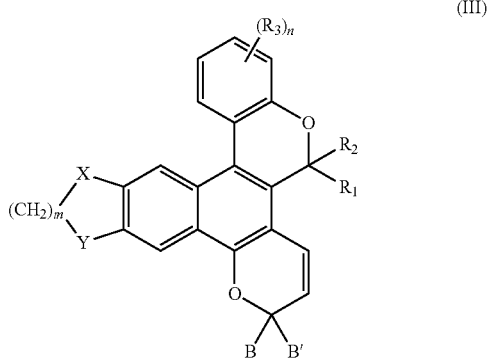
(III)

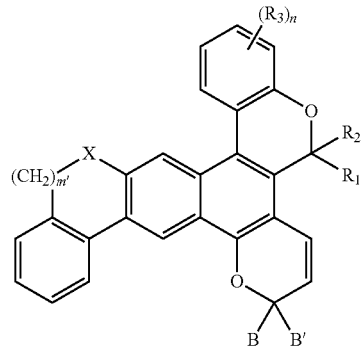
(IV)

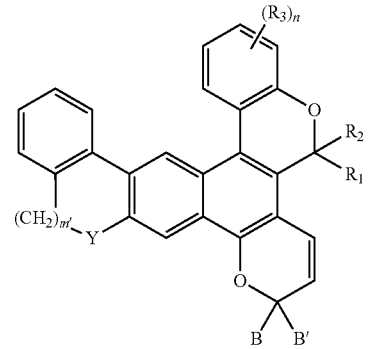
(V)

wherein X and Y are each independently selected from —O—, —$NCH_3$, —$NC_2H_5$, —$NC_6H_5$, —$CH_2$— or —$C(CH_3)_2$—, where the residues $R_1$ to $R_3$, B and B', m and n are as defined in claim 1, above, m' is 0 or 1, with the proviso that either X or Y is oxygen in formula (III).

4. The photochromic naphthopyrans as claimed in claim 3, where X and Y are both —O— in formula (III) and m is 1 or 2.

5. The photochromic naphthopyrans as claimed in claim 3, where X is —O— and Y is —$CH_2$— or —$C(CH_3)_2$— in formula (III), wherein m is 1 or 2.

6. The photochromic naphthopyrans as claimed in claim 3, where X is —$CH_2$— or —$C(CH_3)_2$— in formula (IV) and m' is 0.

7. The photochromic naphthopyrans as claimed in claim 3, where Y is —O— in formula (V) and m' is 1.

8. The photochromic naphthopyrans as claimed in claim 3, where Y is —$NCH_3$, —$NC_2H_5$ or —$NC_6H_5$ in formula (V) and m' is 0.

9. The photochromic naphthopyrans as claimed in claim 1, wherein the residues B and B' are each independently selected from the group a).

10. A plastic material comprising one or more of the photochromic naphthopyrans as claimed in claim 1.

11. The plastic material in claim 10, wherein the plastic material is an ophthalmic lens.

* * * * *